United States Patent [19]

Chandler et al.

[11] Patent Number: 5,731,875
[45] Date of Patent: Mar. 24, 1998

[54] PARTICLE SENSOR WITH FIBER OPTIC CONDUCTOR

[75] Inventors: David L. Chandler, Highland; Raymond J. Felbinger, Mission Viejo; Gerhard Kreikebaum, San Bernardino, all of Calif.

[73] Assignee: Venturedyne, Ltd., Milwaukee, Wis.

[21] Appl. No.: 882,926

[22] Filed: Jun. 26, 1997

Related U.S. Application Data

[63] Continuation of Ser. No. 560,908, Nov. 20, 1995, abandoned.

[51] Int. Cl.$^6$ .......................... G01N 15/02; G01N 21/00
[52] U.S. Cl. .............................. 356/336; 356/338
[58] Field of Search ........................ 356/335–343; 385/146–147, 31, 901

[56] References Cited

U.S. PATENT DOCUMENTS

| | | | |
|---|---|---|---|
| 4,140,395 | 2/1979 | Kreikebaum | 356/336 |
| 4,728,190 | 3/1988 | Knollenberg | 356/336 |
| 4,871,251 | 10/1989 | Preikschat et al. | 356/336 |
| 5,181,082 | 1/1993 | Jeannotte et al. | 356/338 |
| 5,394,489 | 2/1995 | Koch | 385/31 |
| 5,467,189 | 11/1995 | Kreikebaum et al. | 356/336 |

OTHER PUBLICATIONS

Opto Power Corporation—High Power Diode Lasers Brochure, Jul. 1994—4 pages.

*Primary Examiner*—Frank G. Font
*Assistant Examiner*—Jason D. Vierra-Eisenberg
*Attorney, Agent, or Firm*—Jansson, Shupe, Bridge & Munger, Ltd.

[57] ABSTRACT

The new particle sensor is used for assaying particles and includes a light source comprising one or a plurality of light-emitting laser diodes. Light from each diode propagates along a flexible conduit or "light pipe," preferably a separate fiber optic strand. The sensor has a low voltage power supply and drives the diodes at 1–5 VDC. Light from one or bundled fiber optic strand(s) is focused by a focusing lens to provide an intense light beam for small-particle detection. For improved design flexibility, the light source may be mounted independently of the light beam long axis.

13 Claims, 6 Drawing Sheets

PARTICLE SENSOR WITH FIBER OPTIC CONDUCTOR

RELATED APPLICATION

This application is a continuation of application Ser. No. 08/560,908 filed on Nov. 20, 1995, and now abandoned.

FIELD OF THE INVENTION

This invention relates generally to air quality and, more particularly, to instruments for assaying airborne particulates.

BACKGROUND OF THE INVENTION

Particle counters are used to detect light scattered by particles entrained in a stream of fluid, e.g., in an air stream. Such counters draw air (with particles entrained therein) from a room, for example, and flow such air along a tube and through an illuminated sensor "view volume" to obtain information about the number and size of such particles. Such information results from an analysis of the very small amounts of light reflectively "scattered" by the particle as it moves through the view volume.

Such counters direct the air and accompanying particles through the view volume at a particular flow rate (often measured in cubic feet per minute) from one tube (inlet tube) across an open space (view volume) to another tube (outlet tube). In counters of this type, there is no tube wall (however transparent such wall might otherwise be) to impair light scattering and collecting. In other words, the particle is briefly illuminated by a very-small-diameter light beam as it "flies" through an open space.

Among other uses, particle counters are used to obtain a measure of air quality by providing information as to the number and size of particles present in some specified volume of air, e.g., a cubic meter. Even work environments which appear to human observation to be clean—business offices, manufacturing facilities and the like—are likely to have substantial numbers of microscopic airborne particles. While such particles are not usually troublesome to the human occupants, they can create substantial problems in certain types of manufacturing operations.

For example, semiconductors and integrated chips are made in what are known as "clean rooms," the air in which is very well filtered. In fact, clean rooms are usually very slightly pressurized using extremely clean air so that particle-bearing air from the surrounding environs does not seep in. And the trend in the semiconductor and integrated chip manufacturing industry is toward progressively smaller products.

The disadvantage of known particle counters and sensors becomes manifest when trying to detect very small particles, e.g., 0.1 micron and smaller, and/or when trying to detect particles present in a relatively high-flow-volume, e.g., one cubic foot per minute, air stream. Because the particle is very small and/or because it is moving relatively rapidly (thus passing quickly through the illuminated view volume), such particle reflects and scatters very little light.

An apparent solution involves increasing the intensity of the light beam to increase the quantum of light reflected and scattered by very small and/or fast-moving particles. Such efforts have proven largely counterproductive since a more intense light source produces higher levels of random electronic or "shot" noise. And as the light beam becomes more intense, the quantum of light scattered by gas molecules tends to increase, irrespective of whether a particle is also present in the view volume. Shot noise and the increasing quanta of light scattered by gas molecules tends to partially or totally obscure the effect of the particle-scattered light.

To complicate matters even further, plasma-type light sources tend to vary in output power during operation, even if only slightly. As a consequence, the quantum of light scattered by gas molecules varies with variations in power. Plasma-type light sources are widely used in particle sensors and form a part of apparatus shown in, e.g., U.S. Pat. Nos. 4,273,443 (Hogg); 4,728,190 (Knollenberg) and 4,798,465 (Knollenberg).

For high powered plasma sources used to detect very small particles at high flow rates, such variations can be of magnitudes much higher than the shot noise or the noise inherent in an electronic detector. These phenomena dramatically limit the attainable sensitivity. An approach to improving such sensitivity involves using "subtract circuits" which subtract an electrical signal representing only noise from a signal representing both noise and light scattered by a particle.

And plasma-type light sources are attended by other design considerations which, in view of the invention, are unnecessary. For example, such sources require high-voltage power supplies—it is not unusual for a plasma source to require on the order of several thousand volts to "strike" and several hundred volts to continue operating.

Another design consideration is that a carefully-designed adjustment and mounting system is required to obtain and maintain the alignment of the plasma light source. Such alignment is important to maximize the energy at the view volume.

Yet another design consideration attending use of plasma light sources is that the locus of the light beam axis is dictated by the position of the relatively-long tube body which forms a part of such a light source. The engineer is afforded very little design flexibility as to relative position of light source and light beam axis. And such tubes are relatively bulky and rather easily misaligned.

Still another fact of plasma-type light sources is that they employ mirrors and what are known as Brewster windows. Both are easily contaminated and may need frequent cleaning.

Plasma-type light sources are expected to have a life of 2 to 3 years in normal operation. While such life has been reasonably acceptable to equipment users, improvement in light source life would be welcomed.

An improved particle sensor which overcomes some of the problems and shortcomings of known particle sensors would be an important advance in the art.

OBJECTS OF THE INVENTION

It is an object of the invention to provide an improved particle sensor overcoming some of the problems and shortcomings of the prior art.

Another object of this invention is to provide a particle sensor having an improved capability to detect very small airborne particles.

Yet another object of this invention is to provide an improved particle sensor which helps detect particles using (in certain embodiments) once-reflected light, thereby improving signal strength.

Another object of this invention is to provide an improved particle sensor which has an extended range for detecting smaller airborne particles.

Yet another object of this invention is to provide an improved particle sensor which requires no noise-subtracting circuitry.

3

Another object of this invention is to provide an improved particle sensor which exhibits substantially steady-state output power.

Another object of this invention is to provide an improved particle sensor which powers its light source at relatively low voltage.

Another object of this invention is to provide an improved particle sensor having increased life.

Still another object of this invention is to provide an improved particle sensor having a smaller size and lighter weight.

Another object of this invention is to provide an improved particle sensor having a less-sophisticated optic system that requires substantially no periodic cleaning.

Still another object of this invention is to provide a particle sensor having component parts that better retain alignment. How these and other objects are accomplished will become apparent from the following descriptions and from the drawings.

SUMMARY OF THE INVENTION

As used herein, the term "particle counter" means an apparatus which, in addition to components such as a housing, mounting hardware, wiring and the like, includes a sensor and is used to count small airborne particles and determine particle size. The term "sensor" means the light source and the "hardware" (e.g., mirror(s), lens, light detector) used to collect light reflected by a particle and to "convert" such reflected light into electronic pulses.

The invention involves a particle counter for assaying an airborne particle and includes a light source for illuminating such particle. In one embodiment, the source includes a plurality of light-emitting laser diodes, preferably mounted on a diode-supporting substrate which may be planar. Light emitted by each laser diode propagates along a separate fiber optic strand to illuminate the particle. More specifically, light propagating along the fiber optic strands is directed to a focusing lens, thereby focusing light at a view volume through which the particle passes as it moves through the sensor.

The new counter is free of a plasma light source and free of a high voltage power supply for such a light source. Most preferably, the new counter is free of a noise-subtracting circuit whereby one electrical signal representing background "noise" is subtracted from another electrical signal representing both background noise and light scattered by the particle.

The new counter also includes a sensor having a light-collecting apparatus with at least one mirror reflecting light scattered by the particle. Any one of several embodiments provides the desired result, i.e., detection of very small particles. In one embodiment, the mirror is an ellipsoidal mirror having a major focal point and the sensor includes a photodetector at the focal point for providing an electrical signal representing light scattered by the particle. (Persons of ordinary skill will recognize that a photodetector is a device that converts energy in one form, e.g., light, to energy in another form, e.g., electricity.) In another embodiment, the mirror is a spherical mirror reflecting light to an aspheric lens arrangement. Yet another embodiment has a plurality of mirrors including at least one Mangin mirror and a generally planar mirror reflecting light to the Mangin mirror.

And the invention may be considered in yet other ways. The new sensor has a plurality of devices, each device emitting light. A power supply provides electrical power to each of the devices at a voltage not greater than 120 volts and, more preferably, at a voltage not greater than 15 to 20 volts DC. Most preferably, the power supply drives the devices at about 5 VDC. (In other words, the new sensor neither needs nor has a high-voltage power supply for a light source as with known sensors using plasma devices as light sources.)

A plurality of light pipes form a bundle and each light pipe extends between a separate device and a bundle terminus. Light propagating along each of the light pipes is directed to a focusing lens adjacent to the terminus for focusing such light at the sensor view volume. The sensor also has apparatus for collecting light scattered by the particle and an apparatus of any one of the types described above is satisfactory.

In a highly preferred embodiment, each light pipe includes a fiber optic strand. In one variant thereof, the bundle is substantially parallel to the axis along which the particle-illuminating beam of light extends. In another variant, the bundle defines a curved path. The sensor is free of a plasma light source and free of electrical wires powering a light source at a voltage in excess of 120 volts.

Another aspect of the invention involves a light source for use in a particle sensor and in a counter using such sensor. Such source includes an electrically-powered device such as a single diode and a flexible light pipe such as a single fiber optic strand directing light from the device to a terminus. In a more specific aspect, the conduit has an input end and light from the device enters the input end and emanates from the terminus. The source is free of a Brewster window (as used with plasma-type sources) and operates at a voltage well less than 120 volts.

Further details of the invention are set forth in the following detailed description and in the drawings.

DETAILED DESCRIPTION OF PREFERRED EMBODIMENT

Figure 1:
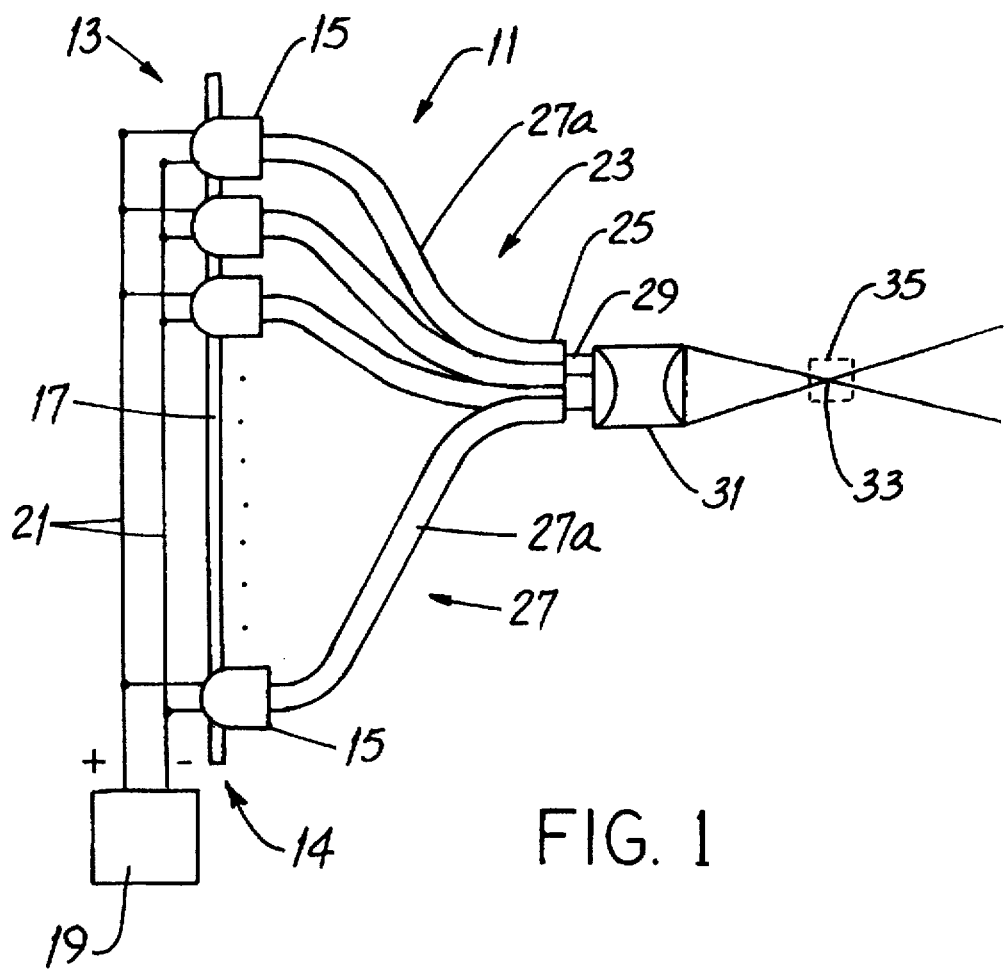
FIG. 1 is a top plan view, greatly enlarged, of one embodiment of a light source including an array of laser diodes.

Before describing the new sensor 10, it will be helpful to have an understanding of aspects of the new light source 11 used in such sensor 10. Referring first to FIG. 1, the source 11 has an electrically-powered device 13 emitting light. In a preferred embodiment, the device 13 includes an array 14 of laser diodes 15 mounted "in line" on a generally planar supporting substrate 17. (While an in-line array 14 is shown, other arrangements, e.g., a matrix, are possible.) The diodes 15 are connected in parallel to a low-voltage source of electrical power 19, e.g., a 1-5 volts DC power supply.

Figure 2:
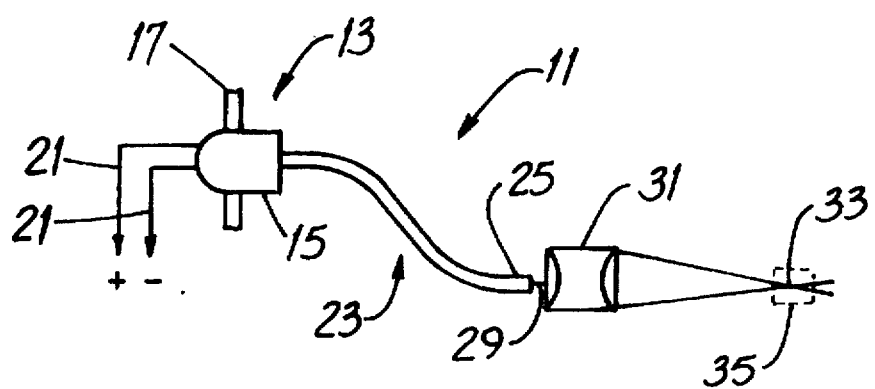
FIG. 2 is a top plan view, greatly enlarged, of another embodiment of a light source including a single laser diode.

In the embodiment of FIG. 2, the device 13 is a single laser diode 15 supported on a substrate 17. Electrical leads 21 connect such diode 15 to a source of electrical power 19. (While single laser diodes 15 having the required power, e.g., on the order of 20-30 watts, are not known to be now available, their development seems to be likely. The invention contemplates such a development.)

The source 11 also has a flexible conduit 23 directing the light from the device 13 to a terminus 25. In the preferred embodiment, the conduit 23 includes a separate light pipe 27 such as a fiber optic strand 27a which directs light from each diode 15 to the terminus 25. Preferably, the light source 11 also includes a lens 31 at the terminus 25 for focusing light rays 29 from each light pipe to a common focal point 33 at the "view volume" 35 of a particle sensor 10. (Persons of ordinary skill in the art will recognize that as used in connection with a particle sensor 10, the view volume is that spatial region at the intersection of a light beam and the path of a particle travelling through the sensor 10.)

Figure 3:
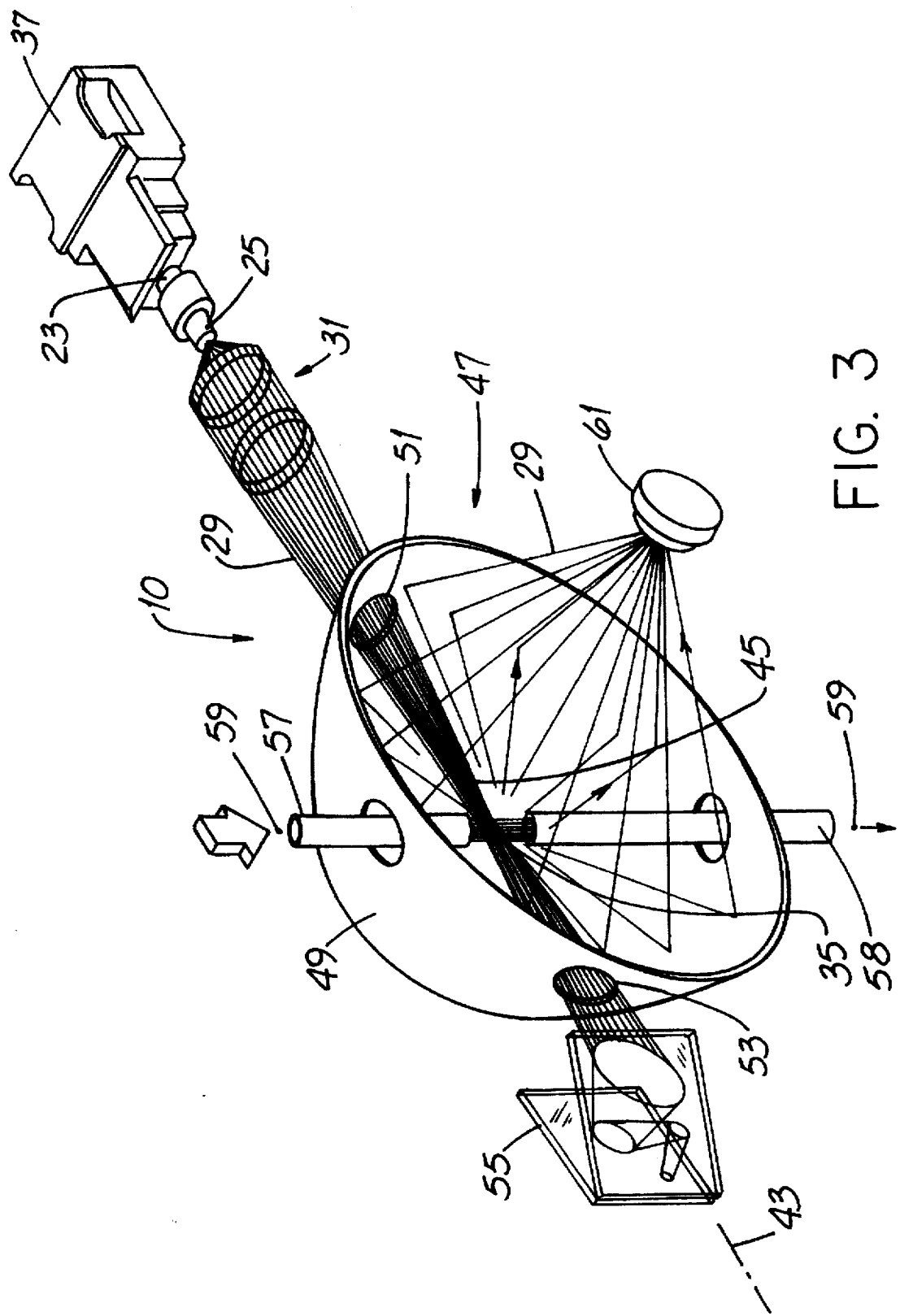
FIG. 3 is a simplified perspective view of one embodiment of the new particle sensor. Parts, e.g., the sensor housing, are omitted and paths of light rays have been separated for clarity.
Figure 7:
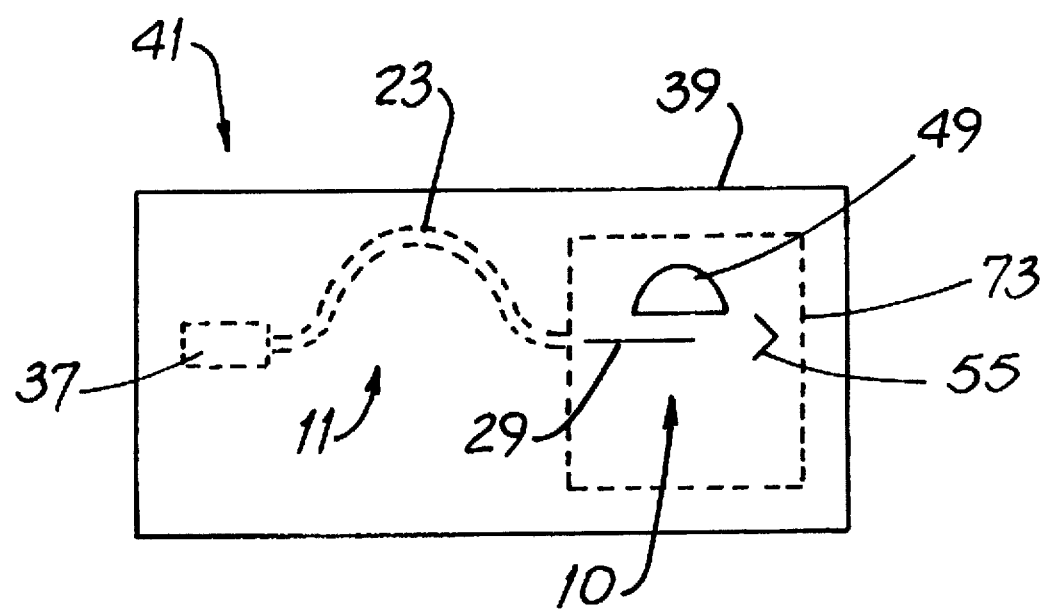
FIG. 7 is a representative view of an instrument cabinet housing a particle sensor and a separately-mounted light source.

Referring also to FIG. 3, one preferred embodiment of the new sensor 10 will now be described. The array-type source 11 of FIG. 1 or the single-diode source 11 of FIG. 2 is within an enclosure 37 configured to be readily mounted within the housing 39 of a particle counter 41. (A housing 39 and counter 41 are shown in FIG. 7 which includes a light source 11 slightly different than that of FIG. 3.) A short conduit 23 of bundled fiber optic strands 27a extends from the enclosure 37 to a terminus 25 where light from each strand 27a emanates to a focusing optic system such as a lens 31. (As used herein, the term "lens" means one or more optical devices for focusing light.) In this embodiment, the conduit 23 and strands 27a are substantially parallel to the beam axis 43.

The lens 31 focuses the light rays 29 to form a light beam 45 which has extremely small diameter and is very intense. The beam 45 is directed to a light collecting apparatus 47 having at least one mirror 49. The apparatus 47 of FIG. 3 includes an ellipsoidal mirror 49 and the beam 45 is directed through an entry opening 51 in the mirror 49, through the sensor view volume 35 (located at the minor focal point of such mirror 49) and out of an exit opening 53 in the mirror 49. Light which is not reflected from a particle to the mirror 49 (as described below) is "killed" by a light trap 55.

Air from a room, the air cleanliness of which is being monitored, is drawn in through the tube 57, flows through the view volume 35 and exits the tube 58 at some flow rate up to about one cubic foot per minute or more. Particles 59 entrained in the air stream fly through the view volume 35 and intersect the light beam 45. Each particle 59 reflects light rays to the mirror 49 and thence to a photodetector 61 at the major focal point of the mirror 49. The resulting electrical output signal from the sensor 10 is analyzed to develop information relating to particle size and number.

Figure 4:
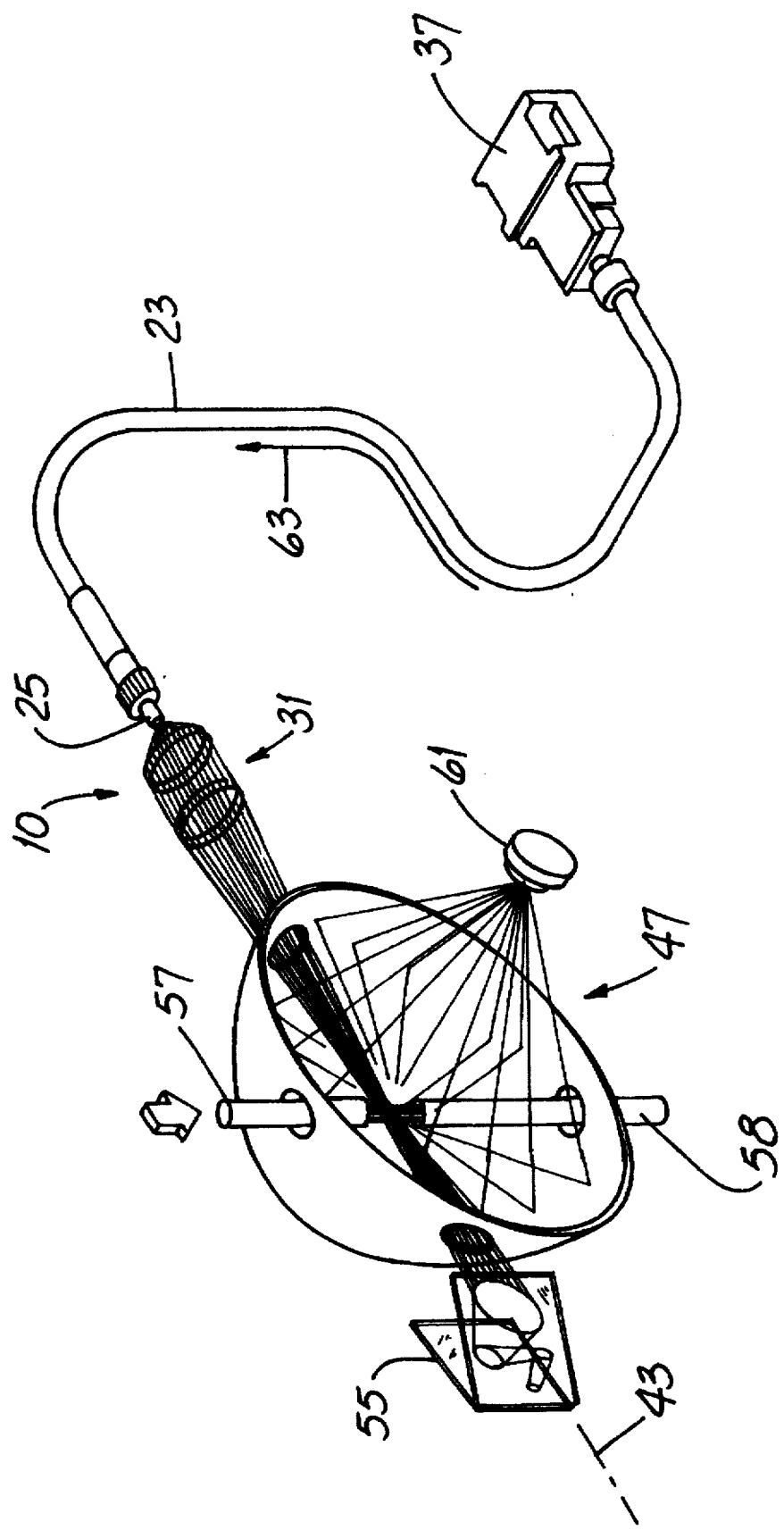
FIG. 4 is a simplified perspective view of another embodiment of the new particle sensor. Parts are omitted and paths of light rays have been separated for clarity.

In the embodiment of FIG. 4, a longer conduit 23 and one or more fiber optic strands 27a forming such conduit 23 define a curved path as represented by the arrow 63. Of course, the strands 27a are not parallel to the beam axis 43 over the entirety of their length as is the case in the embodiment of FIG. 3.

Figure 5:
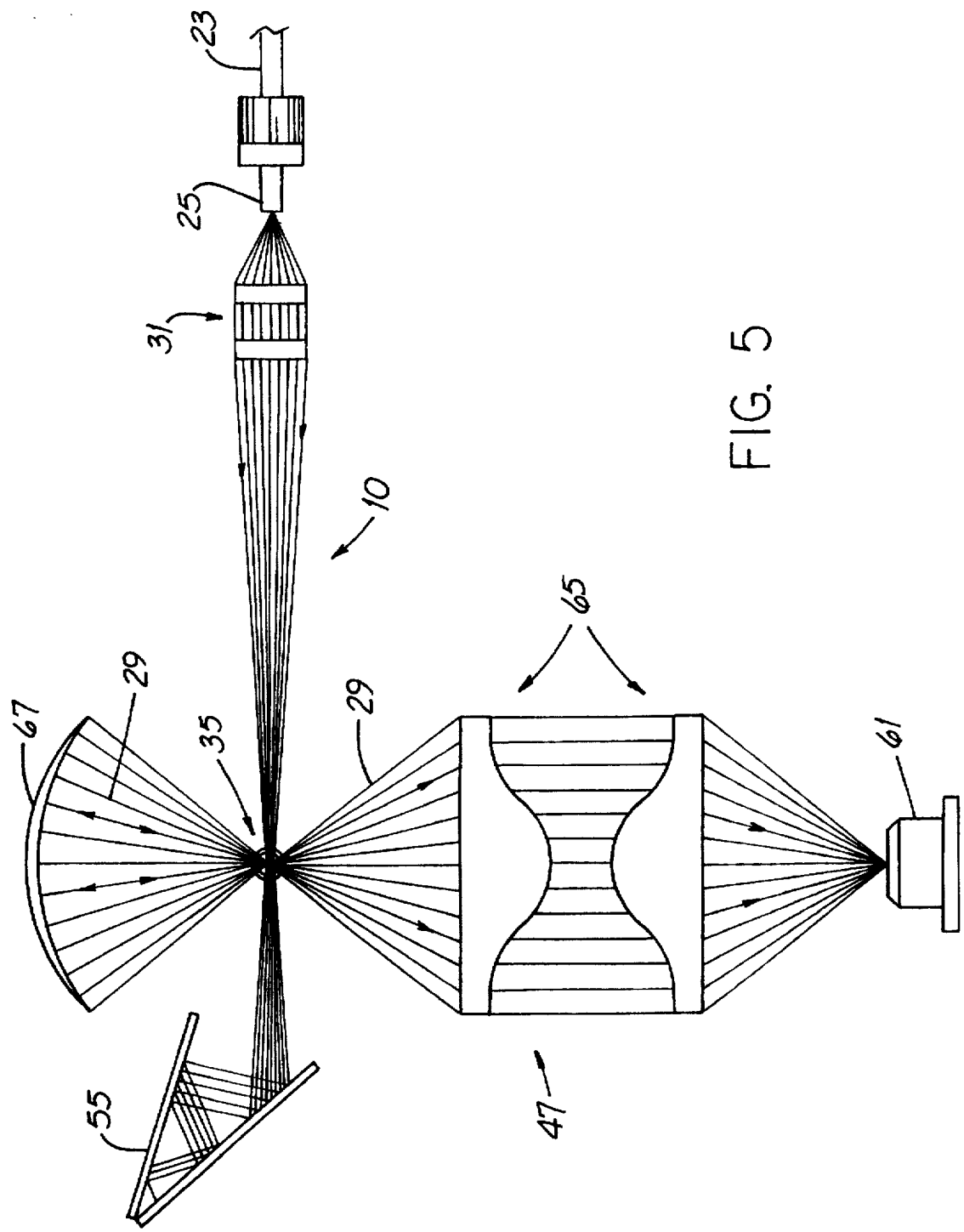
FIG. 5 is a simplified top plan view of yet another embodiment of the new particle sensor. Parts are omitted, other parts are broken away and paths of light rays have been separated for clarity.
Figure 6:
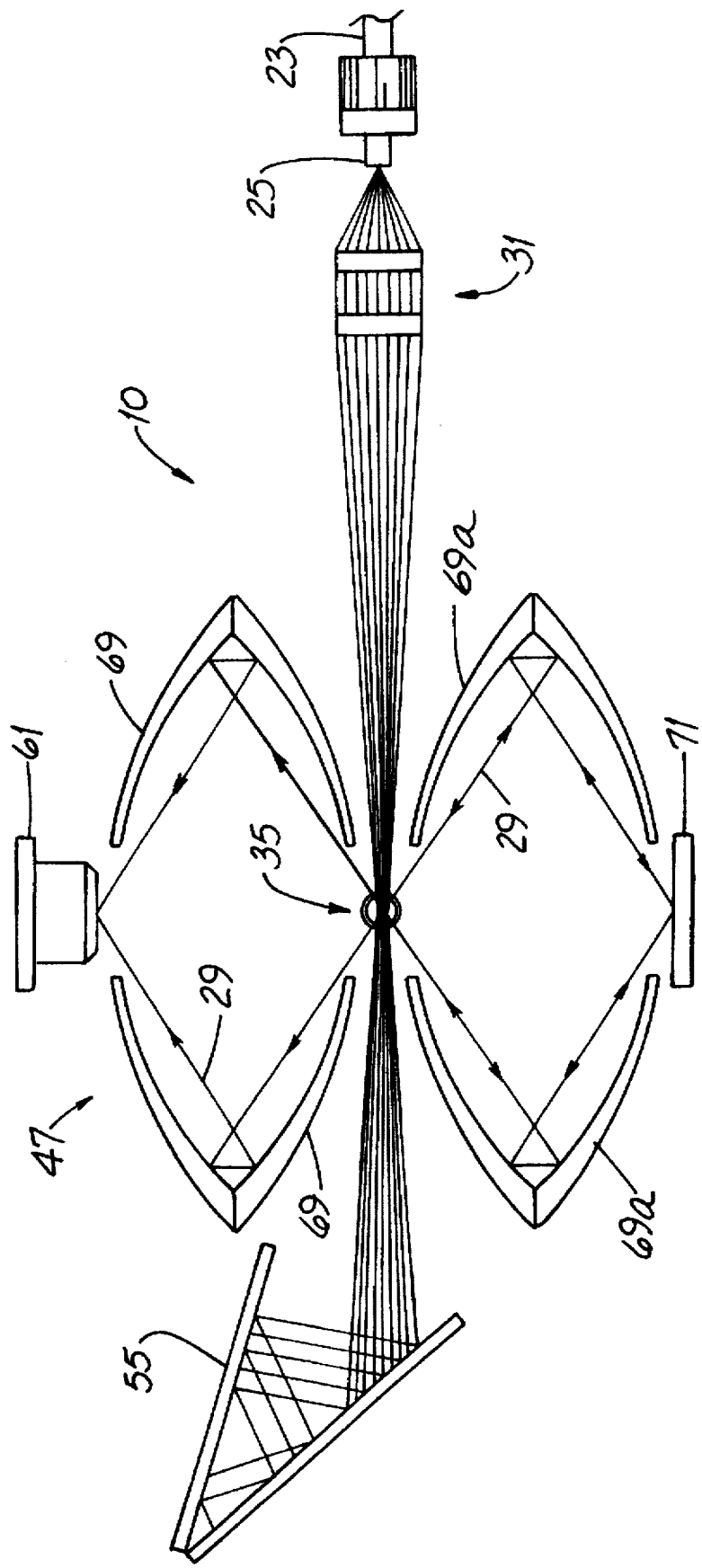
FIG. 6 is a simplified top plan view of still another embodiment of the new particle sensor. Parts are omitted, other parts are broken away and paths of light rays have been separated for clarity.

FIGS. 5 and 6 depict other arrangements for a light collecting sensor 10 with which the new light source 11 may be used. In the arrangement of FIG. 5, light rays 29 reflected downwardly (as viewed in FIG. 5) by a particle 59 in the view volume 35 is focused by an aspheric focusing lens 65. Such focused light is sensed by a light detector 61, the electrical output signal of which is analyzed as described above. Light rays 29 reflected upwardly by a particle in the view volume 35 strikes a spherical mirror 67 which re-directs such light rays 29 to the aspheric focusing lens 65.

The light collecting apparatus 47 of FIG. 6 includes a set of Mangin mirrors 69 collecting light rays 29 reflected upwardly (as shown in the drawing) by a particle 59 in the view volume 35. Such light rays 29 are reflectively directed to a light detector 61. Light rays 29 reflected downwardly by the particle 59 is reflected by a planar mirror 71 coacting with a second set of Mangin mirrors 69a which reflectively re-direct such light rays 29 to the first set of Mangin mirrors 69 and thence to the detector 61.

The matter of design flexibility is also exemplified by FIG. 7. In the representation, an instrument cabinet 73 in the counter 41 houses a particle sensor 10 sans light source 11. A separately-mounted light source 11 has its enclosure 37 mounted away from the cabinet 73. Heat radiating from the enclosure 37 is thereby isolated from the sensor 10. Light from the enclosure 37 is directed along the light conduit 23 to the sensor 10.

As used in this specification, an "array" means a grouping of two or more "light emitters," e.g., diodes 15, each electrically-powered and emitting light.

While the principles of the invention have been shown and described in connection with but a few embodiments, it is to be understood clearly that such embodiments are exemplary and not limiting.

What is claimed:

1. In a particle sensor for determining the size of a particle and including a sensor housing, an air stream flowing in the housing and a light source for illuminating the particle carried by the air stream, the improvement wherein:

the source includes a plurality of light-emitting laser diodes mounted on a single substrate to form an array;

a plurality of separate fiber optic strands, each of the strands conducts light emitted by a separate one of the respective laser diodes;

the fiber optic strands are formed into a bundle to concentrate the light from the light source at a view volume in the air stream and in the housing by emitting light to a bundle terminus which directs the light to at least one stationary lens which focuses the light at the view volume;

light emitted by the bundle is projected along a beam axis and illuminates the particle, causing light scattering;

the sensor includes a light collecting apparatus having at least one optical element collecting the scattered light;

the optical element is selected from a group of optical elements including (a) a spherical mirror, (b) an aspheric lens, (c) an ellipsoidal mirror, and (d) a Mangin mirror; and the light collecting apparatus directs the collected scattered light to a light detector.

2. The sensor of claim 1 wherein the fiber optic strands are substantially parallel to the axis.

3. The sensor of claim 1 wherein each of the fiber optic strands defines a straight path.

4. The sensor of claim 1 wherein such sensor is free of a plasma light source.

5. The sensor of claim 1 wherein such sensor is free of a high voltage power supply powering the light source.

6. The sensor of claim 1 wherein the optical element is an ellipsoidal mirror having a major focal point and the light detector is at the focal point for providing an electrical signal representing light scattered by the particle.

7. The sensor of claim 1 wherein the optical element includes a spherical mirror reflecting light to at least one aspheric lens.

8. The sensor of claim 1 wherein the optical element includes:

at least one Mangin mirror.

9. In combination, an airborne particle and a particle counter having a housing, such counter being for determining the presence of the particle moving in a straight air stream in the housing, the combination further including:

at least two devices mounted with respect to the housing, each device emitting light;

a power source connected to the devices and providing electrical power thereto at a voltage not greater than 120 volts;

a plurality of light pipes forming a bundle, each light pipe extending between a separate device and a bundle terminus and each light pipe having light propagating therealong;

a stationary lens adjacent to the terminus for focusing light propagating along the light pipes, such light extending along a light beam axis and being focused at a view volume in the air stream;

an air flow tube in the housing, orthogonal to the beam axis and carrying the air stream;

a light trap receiving the light from the lens; and a light-collecting sensor between the lens and the light trap and having at least one optical element directing light scattered by the particle, such light being directed to a detector.

10. The combination of claim 9 wherein each light pipe includes a fiber optic strand.

11. The combination of claim 10 wherein:

the bundle is substantially parallel to the light beam axis.

12. The combination of claim 10 wherein the bundle defines a curved path.

13. The combination of claim 9 wherein the particle counter is free of a Brewster window.

* * * * *